United States Patent
Deck (10) Patent No.: US 10,856,864 B2
(45) Date of Patent: Dec. 8, 2020

(54) SUTURING INSTRUMENT CARTRIDGE WITH ENTANGLED SUTURE RELIEF FEATURE

(71) Applicant: Ethicon LLC, Guaynabo, PR (US)

(72) Inventor: Andrew C. Deck, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 143 days.

(21) Appl. No.: 16/012,896

(22) Filed: Jun. 20, 2018

(65) Prior Publication Data

US 2019/0388088 A1 Dec. 26, 2019

(51) Int. Cl.
*A61B 17/06* (2006.01)
*A61B 17/04* (2006.01)

(52) U.S. Cl.
CPC .... *A61B 17/06133* (2013.01); *A61B 17/0482* (2013.01); *A61B 17/0483* (2013.01); *A61B 17/0491* (2013.01); *A61B 17/0493* (2013.01); *A61B 17/06066* (2013.01); *A61B 2017/06076* (2013.01)

(58) Field of Classification Search
CPC ........ A61B 17/000234; A61B 17/0469; A61B 17/0482; A61B 17/062; A61B 17/0625; A61B 17/06133; A61B 17/0483; A61B 17/0491; A61B 17/0493; A61B 17/06066; A61B 2017/06076
See application file for complete search history.

(56) References Cited

U.S. PATENT DOCUMENTS

| 5,766,186 | A | * | 6/1998 | Faraz | A61B 17/0469 606/145 |
|---|---|---|---|---|---|
| 8,702,732 | B2 | | 4/2014 | Woodard, Jr. et al. | |
| 9,168,037 | B2 | | 10/2015 | Woodard, Jr. et al. | |
| 9,357,998 | B2 | | 6/2016 | Martin et al. | |
| 9,375,212 | B2 | | 6/2016 | Martin et al. | |
| 9,474,522 | B2 | | 10/2016 | Deck et al. | |
| 9,839,419 | B2 | * | 12/2017 | Deck | A61B 17/0469 |
| 9,888,914 | B2 | * | 2/2018 | Martin | A61B 17/0469 |
| 10,537,322 | B2 | * | 1/2020 | Martin | A61B 17/06133 |
| 2003/0233108 | A1 | * | 12/2003 | Gellman | A61B 17/0469 606/144 |
| 2016/0367243 | A1 | | 12/2016 | Martin et al. | |

* cited by examiner

*Primary Examiner* — Tan-Uyen T Ho
*Assistant Examiner* — Lee O Chedister
(74) *Attorney, Agent, or Firm* — Frost Brown Todd LLC (57) ABSTRACT

A needle cartridge for a surgical suturing instrument includes a cartridge body, a track extending through the cartridge body and defining a circular path, an arcuate needle movably positioned within the track, and a suture thread extending from the arcuate needle. A needle driver operatively connects to the cartridge body and the arcuate needle. The needle driver is configured to orbit the arcuate needle along the circular path. A needle cover is secured to the cartridge body. A clearance channel extends through at least a portion of the cartridge body along the track in communication with the track such that the clearance channel at least partially defines a suture path. The suture path is configured to receive the suture thread extending from the trailing end of the arcuate needle as the arcuate needle moves along the circular path thereby inhibiting the suture thread from obstructing movement of the arcuate needle.

20 Claims, 9 Drawing Sheets

SUTURING INSTRUMENT CARTRIDGE WITH ENTANGLED SUTURE RELIEF FEATURE

BACKGROUND

Sutures may be used in a wide variety of surgical procedures. Manual suturing may be accomplished by the surgeon using a fine pair of graspers to grab and hold a suture needle, pierce the tissue with the needle, let go of the needle, and re-grasp the needle to pull the needle and accompanying suture thread through the tissues to be sutured. Such needles may be curved with the suture attached to the trailing end of the needle.

Some surgical instruments automate at least part of the suturing procedure. Examples of automated suturing instruments are described in U.S. Pat. No. 8,702,732, entitled "Laparoscopic Suturing Instrument with Dual-Action Needle Graspers," issued Apr. 22, 2014, the disclosure of which is incorporated by reference herein; U.S. Pat. No. 9,168,037, entitled "Laparoscopic Suture Device with Asynchronous In-Line Needle Movement," issued Oct. 27, 2015, the disclosure of which is incorporated by reference herein; U.S. Pat. No. 9,357,998, entitled "Circular Needle Applier with Articulating and Rotating Shaft," issued Jun. 7, 2016, the disclosure of which is incorporated by reference herein; and U.S. Pat. No. 9,474,522, entitled "Jawed Cartridge Receiving Assembly for Needle Cartridge," issued Oct. 25, 2016, the disclosure of which is incorporated by reference herein.

While various kinds of suturing instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal", "distal", "upper", "lower", "top", and "bottom" are defined herein relative to an operator or other operator grasping a surgical instrument having a distal surgical end effector. The term "proximal" refers the position of an element closer to the operator or other operator, and the term "distal" refers to the position of an element closer to the surgical end effector of the surgical instrument and further away from the operator or other operator. The terms "top" and "upper" refer to the position of the element closer to a top of the surgical instrument when viewed by the operator from above, and the terms "bottom" and "lower" refers to the position of the element closer to a bottom of the surgical instrument when viewed by the operator from below. As such, proximal and distal portions are generally in longitudinal opposition as described herein, whereas upper and lower portions are generally in transverse opposition as described herein. The term "lateral" is also used herein to describe the lateral direction, which is perpendicular to the transverse direction. Such terms are used below with reference to views as illustrated for clarity and are not intended to limit the invention described herein.

I. OVERVIEW OF EXEMPLARY SURGICAL SUTURING INSTRUMENT

Figure 1:
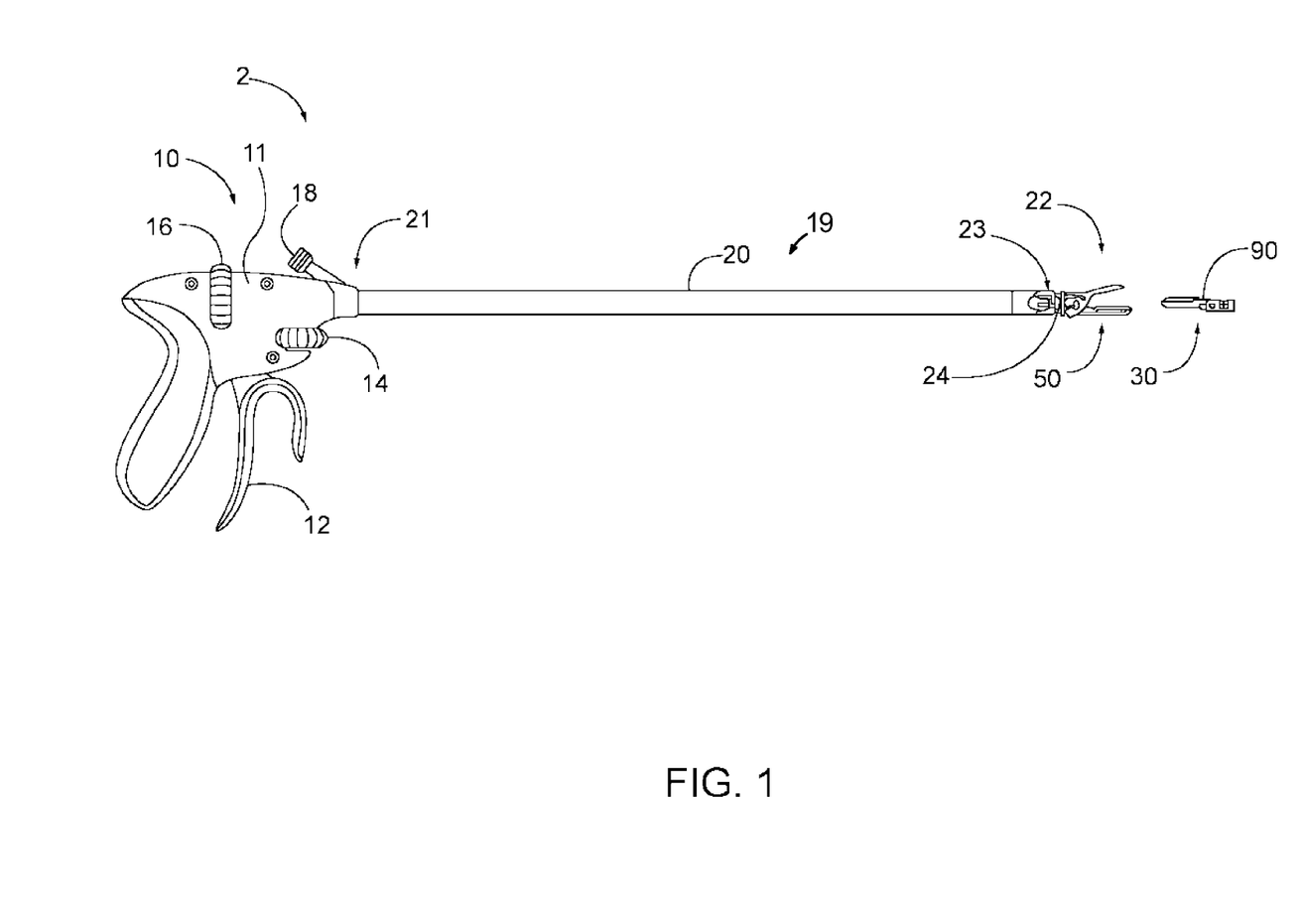
FIG. 1 depicts a side view of an exemplary surgical suturing instrument.

FIG. 1 illustrates an example of a surgical suturing instrument (2). Instrument (2) comprises a handle assembly (10) and a shaft assembly (19) having an elongate shaft (20) extending from a proximal end portion (21) to a distal end portion (22) thereof. Distal end portion (22) includes a cartridge receiving assembly (50), which is operable to receive a first exemplary needle applier cartridge (30), which may also be referred to herein as a needle cartridge (30). Shaft (20) defines a longitudinal axis extending from proximal end portion (21) to distal end portion (22). Handle assembly (10) is connected to proximal end portion (21) of shaft (20). In this example handle assembly (10) is a manual pistol grip handle. However, a variety of other manual actuators could also be used, including but not limited to a scissor grip handle, a syringe grip handle, endoscopic rotary knobs, and the like. Handle assembly (10) could also take the form of a robotic interface, such as a DAVINCI puck, or a housing comprising gears or pulleys, servomechanisms, and the like.

Needle applier cartridge (30) is connected to distal end portion (22) of shaft (20) via cartridge receiving assembly (50). Needle applier cartridge (30) is operable to rotate an arcuate needle in a circular path enabling a surgeon to selectively apply sutures. In some alternative versions, needle applier cartridge (30) is integral with shaft (20) and handle assembly (10) as a unitary disposable instrument intended for a single surgical procedure. Needle applier cartridge (30) may also be integral with shaft (20) and handle assembly (10) as a reusable instrument. Optionally, as illustrated here, needle applier cartridge (30) may be provided in a disposable cartridge body (90) and shaft (20) includes cartridge receiving assembly (50) to releasably hold cartridge body (90). In some such versions, shaft (20) and handle assembly (10) may also be disposable or reusable. Versions with reusable components are intended to be cleaned, sterilized, and reused for multiple surgical procedures, and may include a flush port (18) to facilitate cleaning. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also be used with low temperature sterilization techniques known in the art.

A first user input member (12), shown here as a trigger, pivots between opened and closed positions, may be used to selectively actuate needle applier cartridge (30). The trigger may be spring biased to return the trigger to its open position. A second user input member (14), shown here as a rotary knob, may be used to selectively articulate shaft (20). A third user input member (16), shown here as a rotary knob, may be used to selectively rotate needle applier cartridge (30) about shaft (20). Of course, the number, type, configuration, and operation of first, second, and third input members (12, 14, 16) may vary.

Shaft (20) includes an articulation joint (23). Second user input feature (14) is operable to selectively articulate joint (23) via a joint drive assembly (not shown). Rotary knob (14) rotates in a plane spaced below and generally parallel with shaft (20). An axle (not shown) connects second user input feature (14) to a disk (not shown) in housing (11) that also rotates in a plane generally parallel with the shaft (20) to position distal end portion (22) of shaft assembly (19) relative to proximal end portion (21).

Figure 2A:
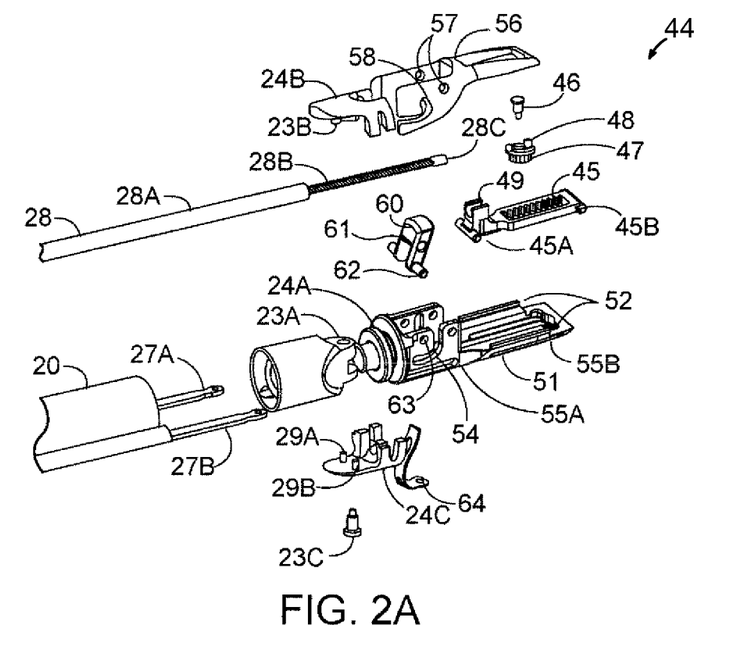
FIG. 2A depicts top perspective exploded view of a cartridge receiving assembly of the instrument of FIG. 1.
Figure 2B:
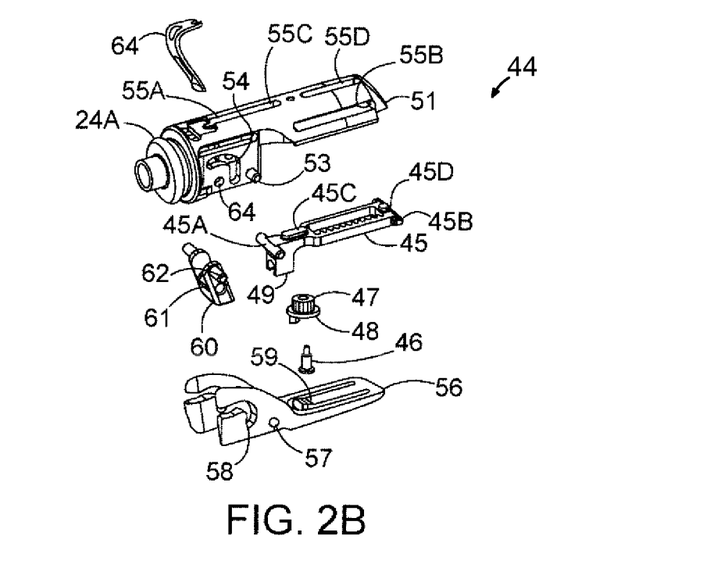
FIG. 2B depicts bottom perspective exploded view of the cartridge receiving assembly of FIG. 2A.

FIGS. 2A-2B illustrate exploded views of cartridge receiving assembly (50) of the present example. Distal end portion (22) of shaft (20) comprises articulation joint (23) and a rotational bearing (24). Articulation joint (23) includes a knuckle (23A) that receives pins (23B, 23C), which are connected to bearing supports (24B, 24C). Thus, pins (23B, 23C) define the pivoting axis for articulation joint (23), enabling cartridge receiving assembly (50) to articulate left and right relative the shaft (20), away from the longitudinal axis defined by shaft (20). Rods (27A, 27B) are operably connected to articulation joint (23). In this example, rods (27A, 27B) extend through shaft (20), through knuckle (23A), and connect to pins (29A, 29B) on bearing support (24C). Rods (27A, 27B) are operatively connected to rotary knob (14) to opposingly push and pull rods (27A, 27B). In other words, second user input feature (14) is operable to drive rods (27A, 27B) at the same time in opposite longitudinal directions, such that rod (27A) will translate distally while rod (27B) translates proximally; and such that rod (27B) will translate distally while rod (27A) translates proximally. Because pins (29A, 29B) are laterally spaced from the pivoting axis, the simultaneous push and pull action will in turn articulate cartridge receiving assembly (50) about joint (23) relative to shaft (20).

Rotational bearing (24) is positioned distal relative to articulation joint (23). Bearing (24) includes a circumferential flange (24A) that is captured between the bearing supports (24B, 24C) such that the flange (24A) can rotate relative the bearing supports (24B, 24C) and enabling unbounded rotation of cartridge receiving assembly (50) relative shaft (20) about the longitudinal axis defined by shaft (20). A drive rod (28) extends through shaft (20). In this example, drive rod (28) comprises a proximal rigid portion (28A) and a distal bendable portion (28B) that are fixedly connected to one another. Bendable portion (28B) extends through articulation joint (23) and through bearing (24); distal end (28C) is fixedly connected to a mount (49) on a rack (45).

Cartridge receiving assembly (50) includes a transmission mechanism (44) configured to transfer force from input trigger (12) to cartridge (30) for actuation thereof. Transmission mechanism (44) includes rack (45) reciprocates longitudinally in lower jaw (51) with followers (45A, 45B, 45C, 45D) constrained in tracks (55A, 55B, 55C, 55D), respectively. Tracks (55A, 55B, 55C, 55D) open through lower jaw (51), providing fluid passages to the internal components within the lower jaw (51), thus facilitating easier cleaning. A pinion (47) is mounted to lower jaw (51) by a pin (46) in the rack (45) such that longitudinal reciprocation of the rack (45) is converted into rotational reciprocation of pinion (47). A key (48) of transmission mechanism (44) communicates the reciprocating rotation to a rotary input (94) in cartridge body (90), which in turn actuates needle applier cartridge (30).

Drive rod (28) is operatively connected to first user input member (12) and to third user input member (16). Actuation of first user input member (12) will impart axial push and pull loads on drive rod (28) to longitudinally reciprocate rack (45) and thereby actuate needle applier cartridge (30). Actuation of third user input member (16) will impart a rotational load on drive rod (28) thus rotating cartridge receiving assembly (50) about bearing (24) relative to shaft (20). Accordingly, a single drive rod (28) operates to both actuate needle applier cartridge (30) as well as control distal rotation of needle applier cartridge (30) about the longitudinal axis of shaft (20). By consolidating dual functions with a single drive rod (28), the number of components is reduced, and more space is provided in the shaft (20), which may make the device less expensive to manufacture and easier to clean.

Cartridge receiving assembly (50) is dimensioned and adapted to receive and hold cartridge body (90). As shown in FIGS. 2A-2B, cartridge receiving assembly (50) of this example has upper and lower jaws (56, 51) that are operable to transition between an open configuration and a closed configuration. In the closed configuration, jaws (56, 51) are operable to receive and retain cartridge body (90). In the closed configuration, jaws (56, 51) are operable to release cartridge body (90). In the present example, lower jaw (51) is stationary and upper jaw (56) pivots. Alternatively, the arrangement could be reversed, or in some versions both jaws (56, 51) could pivot. Lower jaw (51) has two laterally offset longitudinal rails (52) that are dimensioned and adapted to receive cartridge body (90). Rails (52) help longitudinally align cartridge body (90) in cartridge receiving assembly (50) and laterally retain cartridge body (90) in jaws (51, 56). Upper jaw (56) pivots relative lower jaw (51) about a pin (53) that is received in holes (57). A tooth (59) is resiliently oriented downwardly from upper jaw (56) toward lower jaw (51) with a ramped distal face and a stepped proximal face. Tooth (59) is dimensioned and adapted to latch with cartridge body (90) and longitudinally retain cartridge body (90) in jaws (51, 56). Tooth (59) deflects by virtue of a resilient cantilevered arm extending proximally from the distal end of upper jaw (56). In this example, tooth (59) and the cantilevered arm are monolithic with upper jaw (56), thus reducing the number of components and moving pieces, which may make the device less expensive to manufacture and easier to clean.

A button (60) is operable to open and close jaws (51, 56). While button (60) could be placed on or near the handle assembly (10) in some versions, in this example button (60) is positioned adjacent cartridge receiving assembly (50), which eliminates a linkage in shaft (20) thus creating space in shaft (20) and making the device less expensive and easier to clean. The action of button (60) may vary, but in this example button (60) pivots relative to lower jaw (51) about a pin (63) that is received in a hole (61). A follower (62) is received by cam slots (54, 58). Pivoting button (60) proximally will open jaws (51, 56), while pivoting button (60) distally will close jaws (51, 56). A spring (64) engages and biases button (60) distally. By pulling button (60) proximally, follower (62) will drive cam slot (58) to open upper jaw (56). When button (60) is released, spring (64) will resiliently drive button (60) distally to close upper jaw (56).

Figure 3A:
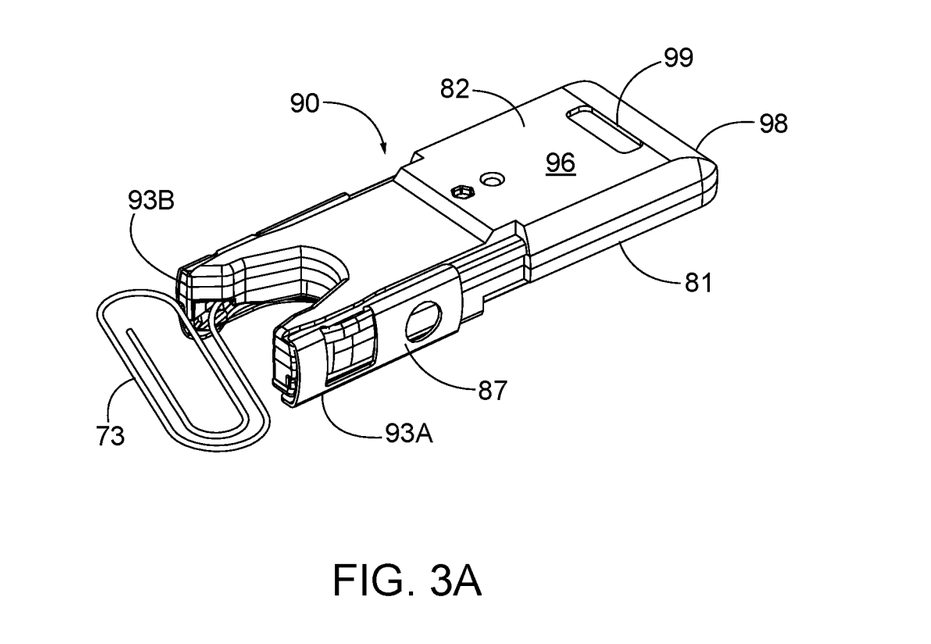
FIG. 3A depicts a top perspective view of a first exemplary needle cartridge configured for receipt in the needle cartridge receiving assembly of FIG. 2A.
Figure 3B:
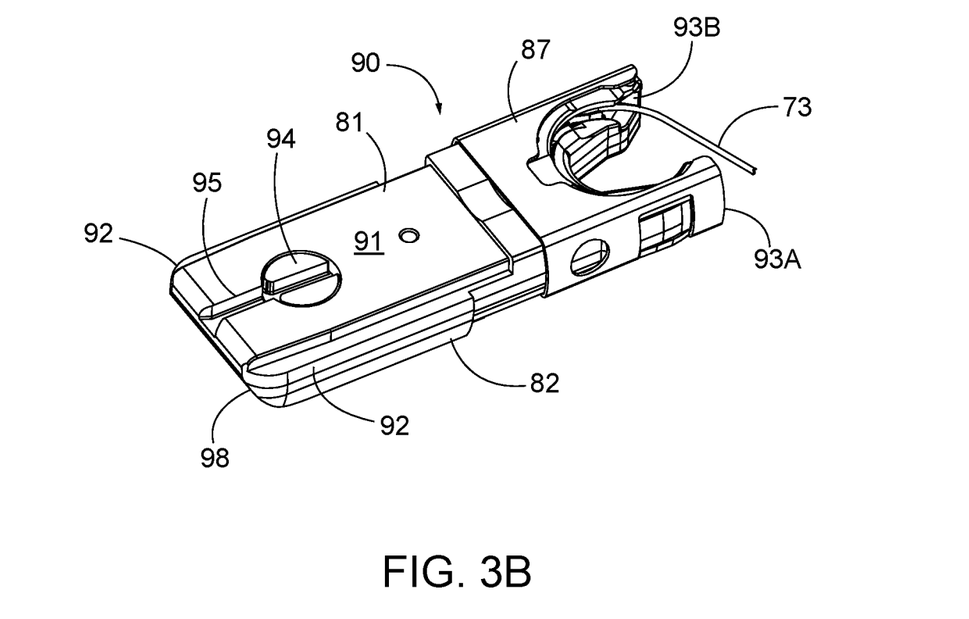
FIG. 3B depicts a bottom perspective view of the needle cartridge of FIG. 3A.

FIGS. 3A-3B illustrate cartridge body (90) of the present example in greater detail. A lower face (91) of cartridge body (90) is adapted to engage lower jaw (51); and an upper face (96) is adapted to engage upper jaw (56). Poke-yoke features on cartridge body (90) prevent improper insertion of cartridge body (90) into cartridge receiving assembly (50), but also contribute to the aesthetic appearance of cartridge body (90). For instance, lower face (91) has a pair of longitudinal notched shoulders (92) that are dimensioned to interface and mate with rails (52). In this example, notched shoulders (92) are shaped as a stepped rabbet, but a variety of other aesthetic shapes could also be employed such as chamfers and radii. In contrast, upper face (96) is asymmetrical relative lower face (91) and lacks shoulder notches, so upper face (96) would interfere with rails (52) if cartridge body (90) were inserted upside-down in cartridge receiving assembly (50). In another instance, the geometry of a proximal face (98) of cartridge body (90) is vertically asymmetrical and thus prevents cartridge body (90) from being inserted upside-down between jaws (51, 56). In this example, proximal face (98) comprises a curved surface that gently transitions to upper face (96), which matches similar geometry in cartridge receiving assembly (50); while the transition to lower face (91) has a tighter radius. Of course, a variety of other asymmetrical aesthetic geometries could also be employed that could contribute to the visual appearance and/or poke-yoke aspects of cartridge body (90).

Arms (93A, 93B) define a generally U-shaped distal end on cartridge body (90). A slot (95) and rotary input (94) are aligned and dimensioned to receive the key (48) while cartridge body (90) is being slid into cartridge receiving assembly (50). When cartridge body (90) is fully seated into cartridge receiving assembly (50), a step (99) aligns with and receives tooth (59) to latch cartridge body (90) in cartridge receiving assembly (50). Key (48) also aligns with rotary input (94), thereby providing a torsional interface that rotationally couples pinion (47) and rotary input (94). In use, the needle (70) exits arm (93A) and enters arm (93B).

Figure 4:
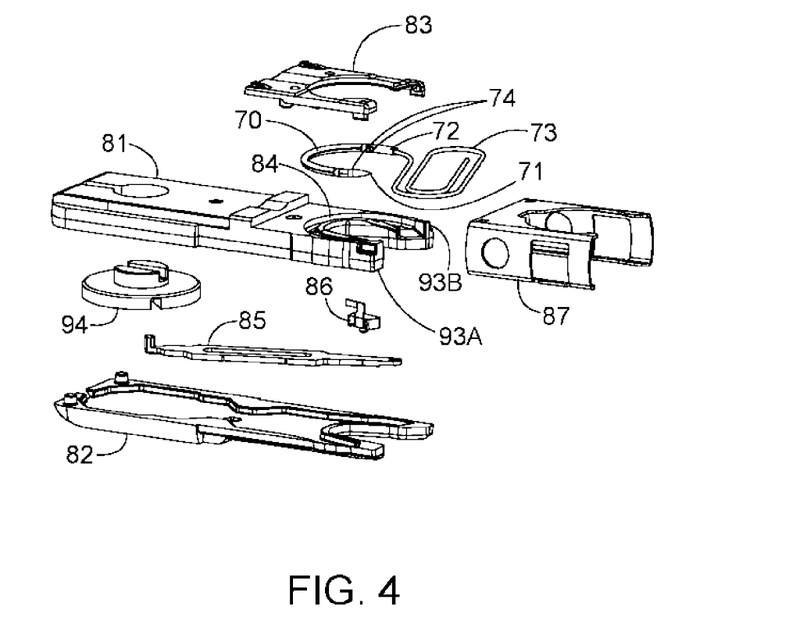
FIG. 4 depicts an exploded view of the needle cartridge of FIG. 3A.

As shown in FIGS. 3A-4, cartridge body (90) further comprises a lower body (81), an upper body (82), a needle (70), a needle cover (83) and a drive assembly (80) configured to drive needle (70). Drive assembly (80) includes a needle driver (86), rotary input (94), and a link (85) are captured between lower body (81) and upper body (82). Bodies (81, 82) may be attached to one another using a variety of known techniques, including welds, pins, adhesives, and the like to form cartridge body (90). Needle (70) has a leading end (71) and a length of suture (73) extending from a trailing end (72) thereof. Needle (70) orbits in a circular path defined by a needle track (84) and between arms (93A, 93B). Needle (70) includes notches (74) that are configured to facilitate engagement between needle driver (86) and needle (70). Needle (70) is captured in needle track (84) by needle cover (83). A cage (87) slides over bodies (81, 82) and needle cover (83) to attach needle cover (83) against lower body (81).

Figure 5A:
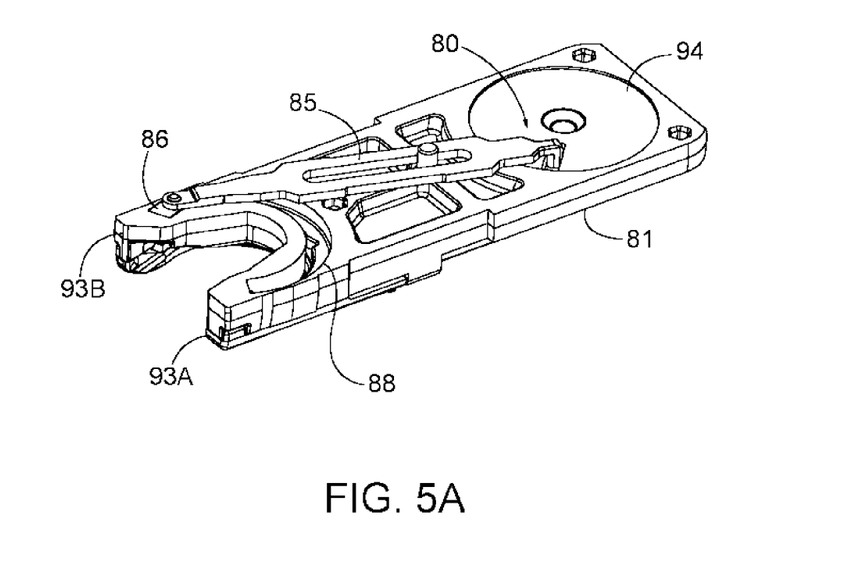
FIG. 5A depicts a perspective view of a drive assembly of the needle cartridge of FIG. 3A, with the drive assembly at one end of its stroke.
Figure 5B:
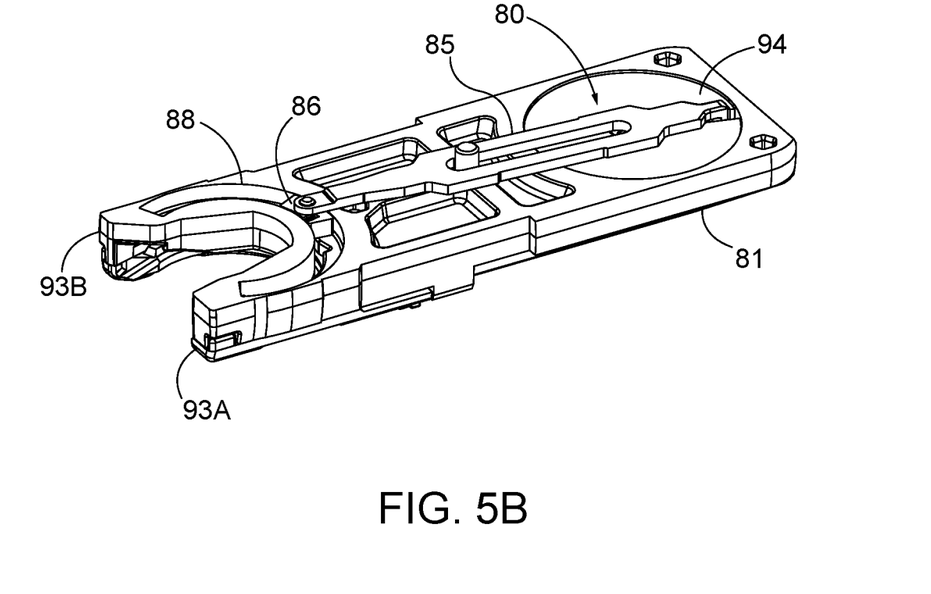
FIG. 5B depicts a perspective view of the drive assembly of FIG. 5A, with the drive assembly at mid-stroke.
Figure 5C:
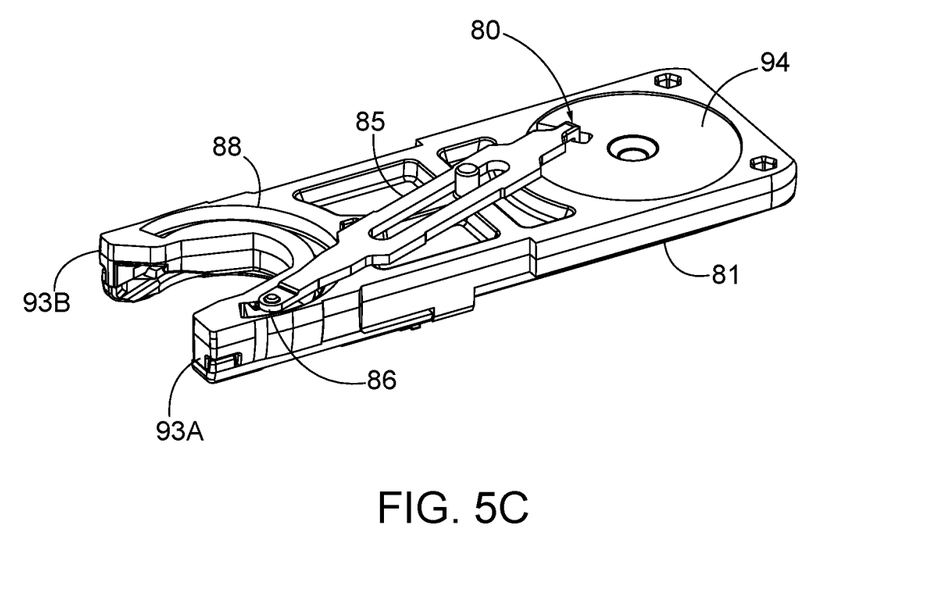
FIG. 5C depicts a perspective view of the drive assembly of FIG. 5A, with the drive assembly at the other end of its stroke.

FIGS. 5A-5C illustrate an example of a drive stroke of the transmission in cartridge body (90) for driving needle (70) in a circular, orbital path. However, it should be understood that needle (70) and suture (73) are omitted from FIGS. 5B-5C for clarity. Needle driver (86) rides in a carrier track (88) and extends into needle track (84) (see FIG. 4) to engage and drive needle (70). Link (85) connects rotary input (94) to needle driver (86). FIG. 5A shows needle driver (86) positioned at one end of its stroke in carrier track (88). As shown in FIG. 5B, counterclockwise rotation of rotary input (94) will translate needle driver (86) clockwise along carrier track (88), thereby driving needle (70) clockwise. As shown in FIG. 5C, continued counterclockwise rotation of the rotary input (94) will continue to translate needle driver (86) and thereby drive needle (70) clockwise until it reaches the other end of its stroke in carrier track (88). In this example, the drive stroke rotates the needle (70) in its circular path along an angular range of about 180 degrees. For the return stroke, the sequence can be reversed by rotating the rotary input (94) clockwise, which will translate needle driver (86) counterclockwise in carrier track (88). Needle driver (86) is disengaged from needle (70) during the return stroke until needle driver (86) reaches the end of the return stroke. Needle driver (86) will re-engage needle (86)

upon completing the return stroke. Thus, a sequence of drive and return strokes will rotate the needle (70) in a circular path.

Figure 6:
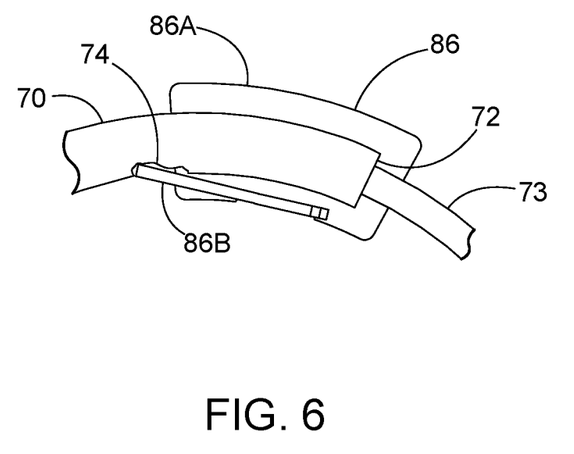
FIG. 6 depicts a partial plan view of a needle driver of the needle cartridge of FIG. 3A engaging a needle of the needle cartridge of FIG. 3A.

FIG. 6 shows a detailed view of needle driver (86) engaging needle (70). Needle driver (86) comprises a carrier (86A) and a driver (86B). Carrier (86A) is dimensioned to slidably fit in carrier track (88). Driver (86B) is attached to carrier (86A) and is operative to engage needle (70) at an oblique angle. Leftward movement of needle driver (86) will cause driver (86B) to engage proximal notch (74) of needle (70) during the drive stroke. When so engaged, needle (70) will slide in needle track (84) in unison with needle driver (86). Due to the oblique angle, rightward movement of needle driver (86) will disengage driver (86B) from proximal notch (74) of needle (70) and slide over the stationary needle (70) during the return stroke.

Referring back to FIGS. 5A-5C and FIG. 6, when first user input member (12) (see FIG. 1) is depressed, closing the trigger, needle driver (86) will be actuated through its drive stroke where it orbits along an angular range of motion at least about 180 degrees counterclockwise to a driven position as shown in FIG. 5C. During the drive stroke, driver (86B) engages proximal notch (74) and will in unison rotate needle (70) about 180 degrees along an orbital path to its extended position. Needle (70) will span across arms (93A, 93B) between exit port (97A) and entrance port (97B). Tissue interposed between arms (93A, 93B) will be pierced by leading end (71) of needle (70).

When first user input member (12) (see FIG. 1) is released and the spring return opens the trigger, needle driver (86) reciprocates through its return stroke where it orbits along an angular range of motion about 180 degrees clockwise back to the return position shown in FIG. 5A. During the return stroke, driver (86B) slides over the needle (70). Driver (86B) is then adjacent the distal notch (74). When first user input member (12) is depressed again closing the trigger, needle driver (86) will again be actuated through its drive stroke where it orbits along an angular range of motion about 180 degrees counterclockwise to the driven position as shown in FIG. 5C. During the drive stroke, driver (86B) engages distal notch (74) and will in unison drive needle (70) orbitally along an angular range of motion about 180 degrees back to its retracted position. Suture (73) (see FIG. 3A) will follow needle (70) and be threaded through the pierced tissue.

When first user input member (12) (see FIG. 1) is again released and the spring return opens the trigger, needle driver (86) again reciprocates through its return stroke where it orbits along an angular range of motion about 180 degrees clockwise back to its returned position as shown in FIG. 5A. During the return stroke, driver (86B) slides over needle (70). Thus, needle (70) is driven in a complete circular path spanning an angular range of 360° in response to first user input member (12) being actuated twice. The sequence may be repeated as needed by the surgeon to achieve the desired suturing task.

Further details, explanations, examples, and alternative embodiments of surgical suturing devices and subcomponents of the foregoing are disclosed in U.S. Pat. No. 9,357,998, entitled "Circular Needle Applier with Articulating and Rotating Shaft," issued Jun. 7, 2016, the disclosure of which is incorporated by reference herein; U.S. Pat. No. 9,474,522, entitled "Jawed Cartridge Receiving Assembly for Needle Cartridge," issued Oct. 25, 2016, the disclosure of which is incorporated by reference herein; U.S. Pat. No. 9,375,212, entitled "Circular Needle Applier with Cleats," issued Jun. 28, 2016, the disclosure of which is incorporated by reference herein; and U.S. Pat. Pub. No. 2016/0367243, entitled "Suturing Instrument with Motorized Needle Drive," published Dec. 22, 2016, issued as U.S. Pat. No. 9,888,914 on Feb. 13, 2018, the disclosure of which is incorporated by reference herein. It should be understood that such details, explanations, examples, and alternative embodiments may be readily applied to the above-described instrument (10) and subcomponents thereof.

II. NEEDLE CARTRIDGE WITH CLEARANCE CHANNEL ALONG A SUTURE PATH FOR SUTURE THREAD

In some instances, it may be desirable for the orbital needle path of the suture cartridge to be sized wide enough to slidably receive sutures of varying dimensions and profiles to minimize instances of the suture being immovably constricted therein. For instance, various suturing procedures may require the use of a particularly sized suture to treat the target size. In some instances, the required suture has a greater diameter and/or cross-sectional profile relative to other suitable sutures. Inserting a suture with a relatively greater diameter into the orbital needle path of the suture cartridge may result in the suture becoming jammed. Accordingly, providing a suture cartridge with an enhanced travel path or needle gap that is sized to accommodate various suitably sized sutures may be beneficial to ensure the suture will freely translate along the needle gap without encountering any restrictive impediments. However, enhancing the size of the needle gap may result in the needle received therein to prematurely exit the needle gap due to the comparatively smaller size of the needle relative to the orbital path. Accordingly, it may be desirable to provide additional suture clearance to receive the suture adjacent to needle (70) and inhibit needle (70) from becoming jammed during use. An example of such clearance is a clearance channel (110) discussed below. To this end, like numbers below indicate like features described above. Of course, other such channels may be similarly used such that the invention is not intended to be unnecessarily limited to the particular clearance channel (110) shown and described herein. Other suitable ways in which various surgical suturing instruments may be used will be apparent to those of ordinary skill in the art in view of the teachings herein.

Figure 7:
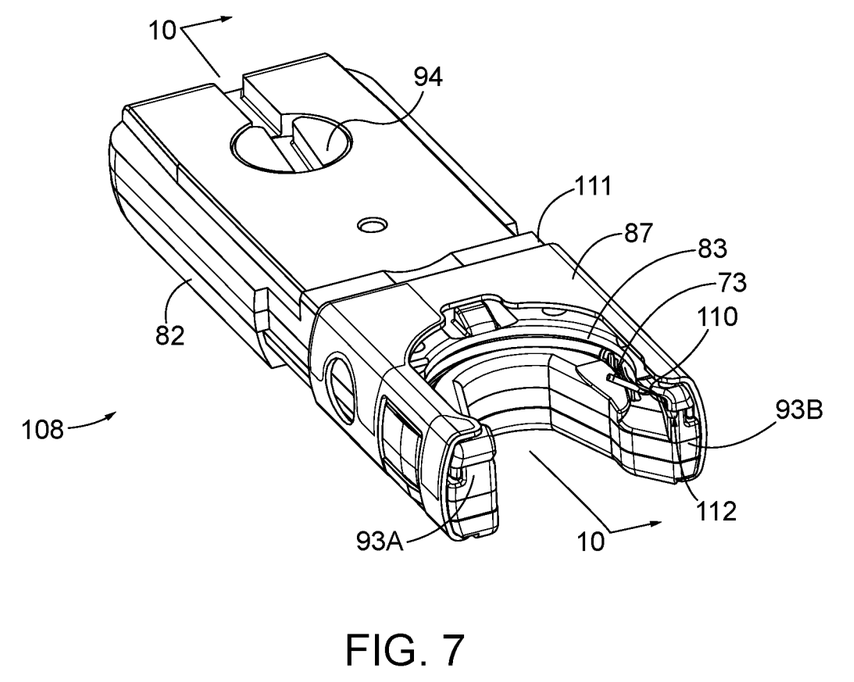
FIG. 7 depicts a perspective view of a second exemplary needle cartridge.
Figure 8:
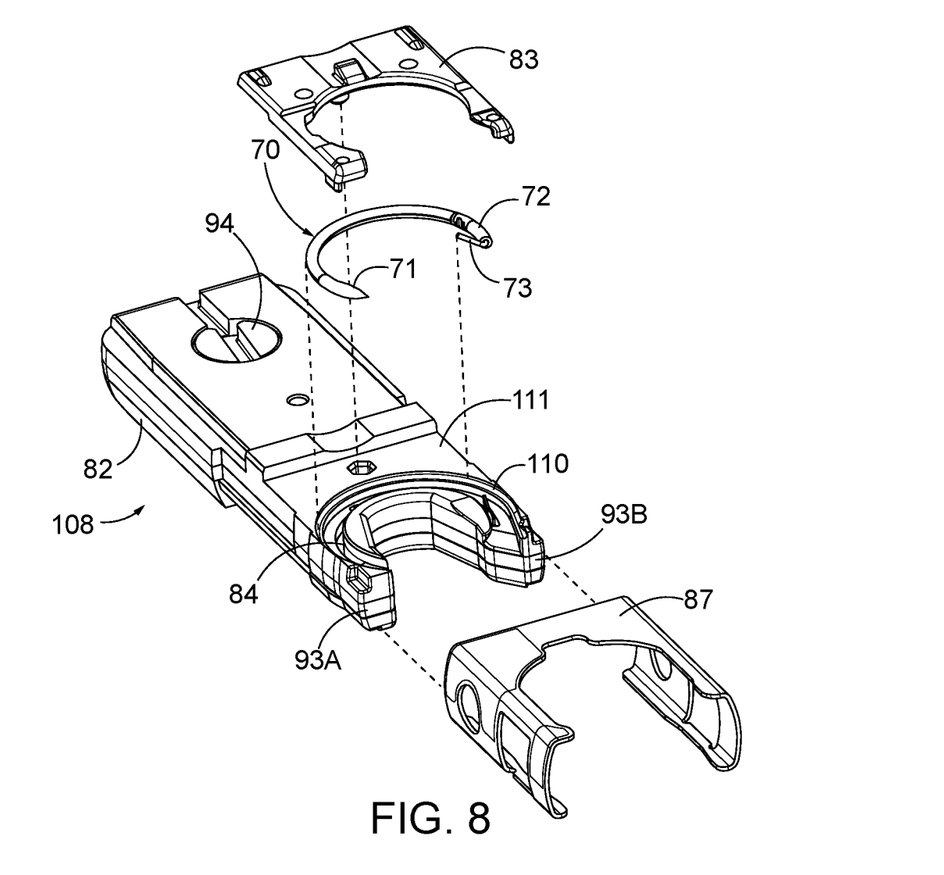
FIG. 8 depicts a partially exploded perspective view of the needle cartridge of FIG. 7 including an arcuate needle, a needle cover, a cage, and a cartridge body having a clearance channel configured to inhibit suture blockage.

FIGS. 7-8 show a second exemplary needle cartridge (108) having arcuate needle (70) received in circular needle track (84) extending between arms (93A, 93B) of a cartridge body (111). Cage (87) and needle cover (83) retain needle (70) in needle track (84) as discussed above in greater detail. In addition, clearance channel (110) extends along needle track (84) in communication with needle track (84) to provide clearance for suture thread (73) along a suture path (112) in the event that needle (70) pulls suture thread (73) into needle track (84) during use. Thereby, clearance channel (110) inhibits suture thread (73) from blocking passage of needle (70) through needle track (84).

Figure 9:
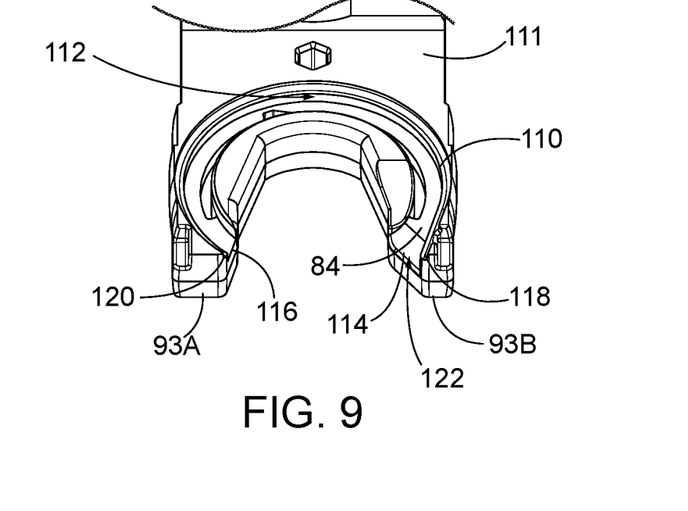
FIG. 9 depicts a distal end perspective view of the clearance channel within the cartridge body of FIG. 8.

With respect to FIGS. 8-9, clearance channel (110) is positioned radially outward from and adjacent to needle track (84) such that clearance channel (110) surrounds needle track (84). More particularly, needle track (84) has a track inlet opening (114) through a distal end of arm (93B) and a track outlet opening (116) through a distal end of arm (93A). Clearance channel (110) similarly has a clearance inlet opening (118) through a distal end of arm (93B) and a clearance outlet opening (120) through a distal end of arm (93A). Clearance inlet opening (118) is positioned radially outward from and adjacent to track inlet opening (114) in direct communication with track inlet opening (114) such that trailing end (72) of needle (70) is configured to be introduced into needle track (84) through track inlet opening (114). In the event that needle (70) pulls suture thread (73) into needle track (84) during use, suture thread (73) is displaced by the needle into clearance channel (110) to provide ample space for needle (70) to rotate in needle track (84) while suture thread (73) is pulled along clearance channel (110) so as not to functionally obstruct needle (70) with suture thread (73). Clearance outlet opening (120) is positioned radially outward from and adjacent to track outlet opening (116) in direct communication with track outlet opening (116) such that trailing end (72) of needle (70) discharges from needle track (84) through track outlet opening (116). In turn, suture thread (73) discharges from clearance outlet opening (120) during subsequent firing of the needle (70). Given that suture thread (73) extends from trailing end (72) of needle (70), the entirety of clearance channel (110) is in direct, radial communication with needle track (84) to allow suture thread (73) to extend from track (84) and into clearance channel (110).

Figure 10:
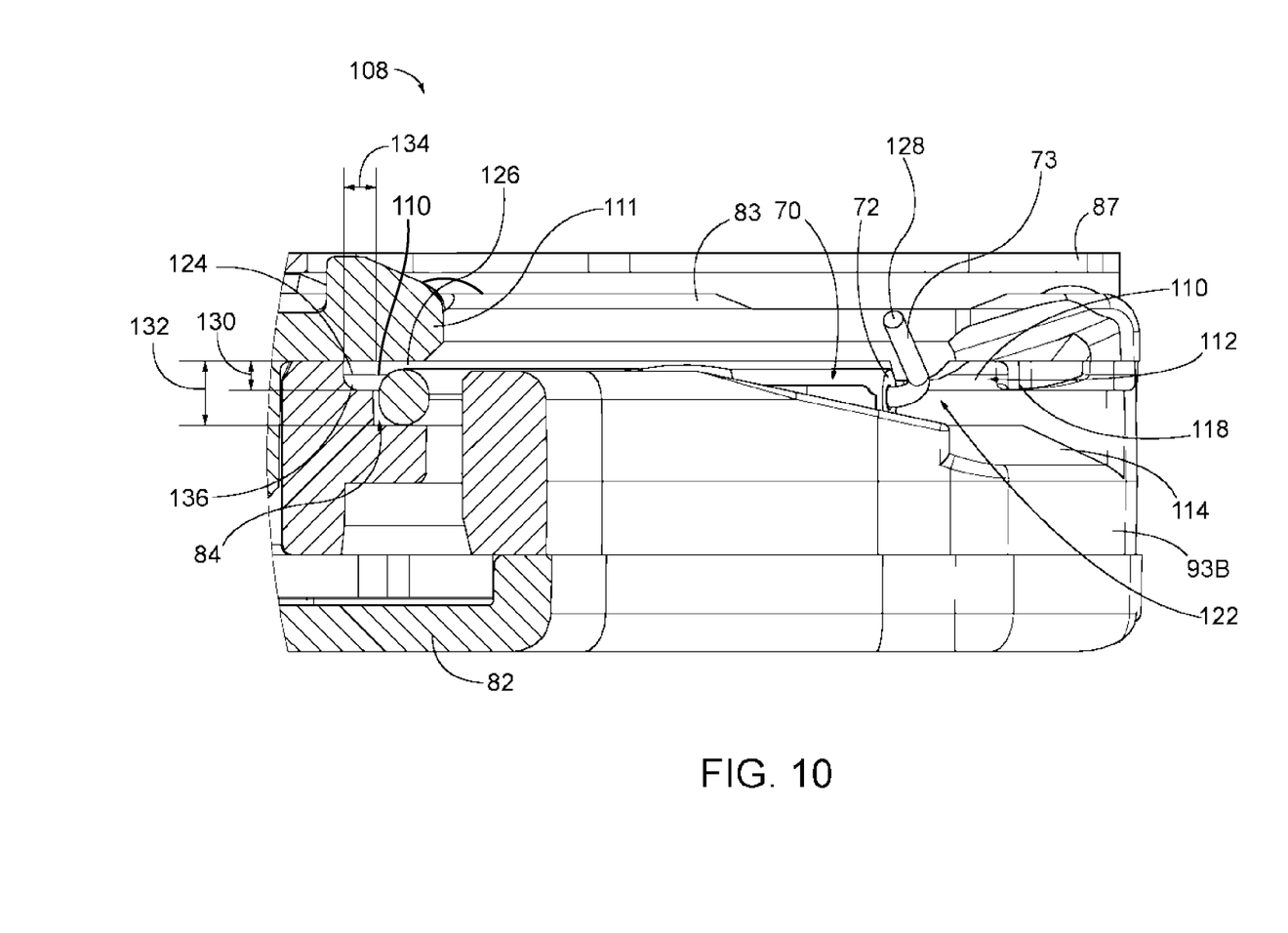
FIG. 10 depicts an enlarged, cross-sectional view of the needle cartridge of FIG. 7 taken along section line 10-10 of FIG. 7.

FIG. 10 shows clearance channel (110) of the present example in relation to needle track (84) in greater detail. Needle cover (83) releasably secures against cartridge body (111) to define a circular path (122) between needle cover (83) and cartridge body (111) along needle track (84) as discussed above in greater detail. Needle (70) thus orbits along circular path (122) in an orbital plane. Similarly, suture path (112) is defined between needle cover (83) and cartridge body (111) in clearance channel (110), which surrounds circular path (122) in a channel plane. Channel plane is parallel with and offset from orbital plane in the present example, but may be alternatively angled in other examples such that clearance channel (110) receives and guides suture thread (73) therethrough during use.

To this end, suture path (112) has a radial cross-sectional suture gap area (124) taken along a radius about circular path (122) while circular path has a radial cross-sectional path area (126) taken along that same radius as shown in the plane of FIG. 10. Suture thread (73) similarly has a transverse cross-sectional thread area (128) that is perpendicular to a centerline through suture thread (73). Transverse cross-sectional thread area (128) is also taken along that same radius shown in the plane of FIG. 10 in the present example, but may move depending on the position of suture thread (73). Radial cross-sectional path area (126) is greater than radial cross-sectional suture gap area (124) in order to receive needle (70) therealong. In contrast, radial cross-sectional suture gap area (124) is greater than or substantially similar to transverse cross-sectional thread area (128) such that suture path (112) may receive suture thread (73) to inhibit functionally obstructing circular path (122). More particularly, radial cross-sectional suture gap area (124) is substantially similar to transverse cross-sectional thread area (128) such that suture path (112) receives suture thread (73) to inhibit functionally obstructing circular path (122) as shown in FIG. 10. However, clearance channel (110) has a suture gap height (130) less than one-half of a needle gap height (132) to thereby properly retain needle (70) in track (84) while orbiting. In the present example, clearance channel (110) also has a suture gap width (134) approximately equal to suture gap height (130) with a chamfered edge (136) extending therebetween. By way of example, clearance channel (110) is continuous about track (84) such that suture gap height (130), suture gap width (134), and radial cross-sectional suture gap area are uniform along an entirety of clearance channel (110). Alternatively, clearance channel (110) may vary to guide suture thread (73) as desired, and the invention is not intended to be unnecessarily limited to the particular dimensions shown in the present example.

Figure 11A:
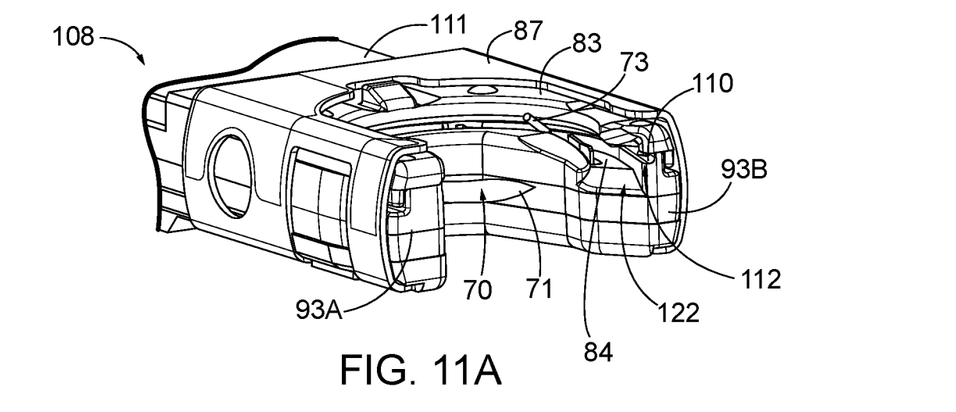
FIG. 11A depicts a distal end perspective view of the needle cartridge of FIG. 7 with a leading end of the arcuate needle departing a needle track for reintroduction into the needle track.
Figure 11B:
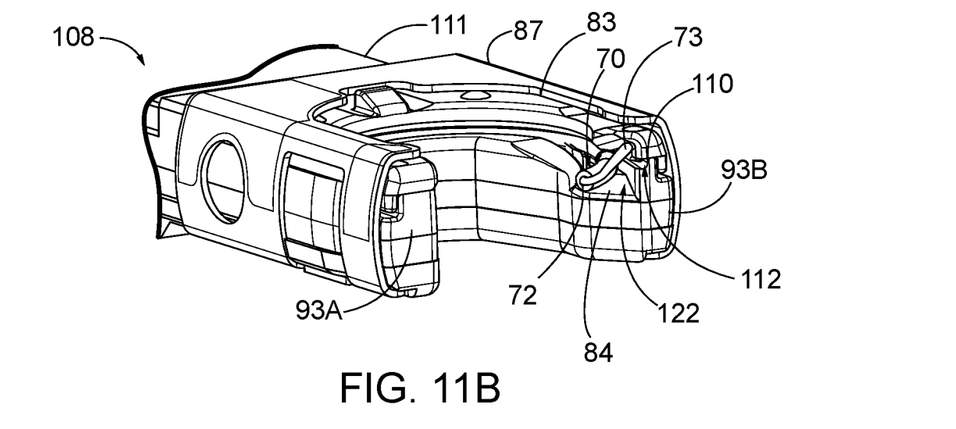
FIG. 11B depicts the distal end perspective view of the needle cartridge similar to FIG. 11A, but showing a trailing end of the arcuate needle with suture thread attached thereto being reintroduced into the needle track.
Figure 11C:
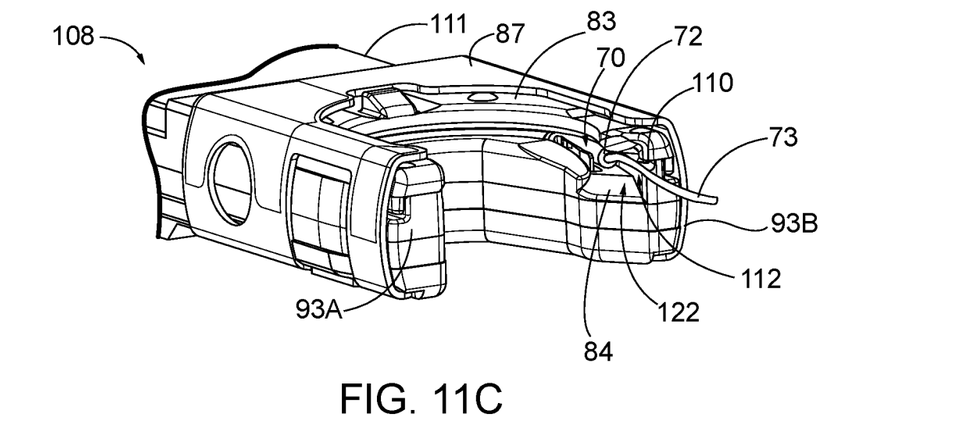
FIG. 11C depicts the distal end perspective view of the needle cartridge similar to FIG. 11B, but showing the suture thread following the trailing end of the arcuate needle through the needle track and into the clearance channel thereby inhibiting the suture thread from blocking passage of the arcuate needle through the needle track.

In use, with respect to FIG. 11A, leading end (71) of needle (70) discharges from track outlet opening (116) of track (84) to pierce and suture tissue (not shown) between arms (93A, 93B). Needle (71) orbits to introduce leading end (71) into track inlet opening (114) followed by trailing end (72) with suture thread (73) attached thereto as shown in FIG. 11B. On occasion while orbiting, suture thread (73) is pulled into track (84). However, rather than wedge against needle (70), suture thread (73) extends from track (84) and into clearance channel (110) of suture path (112). FIG. 11C shows clearance channel (110) receiving and guiding suture thread (73) while needle (70) simultaneously orbits to inhibit suture thread (73) from obstructing movement of needle (70). While some frictional engagement may occur between suture thread (73), needle (70), and/or cartridge body (111) while orbiting needle (73), such frictional engagement is reduced in the present example to so as to inhibit deformation of needle (73) and provide for sufficient operative movement of needle (73). It will be appreciated that some engagement and compression may be applied to needle (73) in accordance with the present example.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A needle cartridge for a surgical suturing instrument, the needle cartridge comprising: (a) a cartridge body; (b) a track extending through at least a portion of the cartridge body and at least partially defining a circular path; (c) an arcuate needle movably positioned within the track and having a leading end and a trailing end; (d) a suture thread extending from the trailing end; (e) a needle driver operatively connected to the cartridge body and the arcuate needle, wherein the needle driver is configured to orbit the arcuate needle along the circular path; (f) a needle cover secured to the cartridge body and configured to releasably retain the arcuate needle with the track; and (g) a clearance channel extending through at least a portion of the cartridge body along the track in communication with the track such that the clearance channel at least partially defines a suture path, wherein the suture path is configured to receive the suture thread extending from the trailing end of the arcuate needle as the arcuate needle moves along the circular path thereby inhibiting the suture thread from obstructing movement of the arcuate needle.

Example 2

The needle cartridge of Example 1, wherein the track includes a track inlet opening, wherein the leading end of the arcuate needle is configured to be introduced into the track through the track inlet opening, wherein the clearance channel includes a clearance inlet opening configured to receive the suture thread therein, wherein the clearance inlet opening is positioned adjacent to the track inlet opening such that the clearance inlet opening is in direct communication with the track inlet opening.

Example 3

The needle cartridge of Example 2, wherein the track further includes a track outlet opening, wherein the trailing end of the arcuate needle is configured to be discharged from the track through the track outlet opening, wherein the clearance channel further a clearance outlet opening configured to discharge the suture thread therefrom, and wherein the clearance outlet opening is positioned adjacent to the track outlet opening such that the clearance outlet opening is in direct communication with the track outlet opening.

Example 4

The needle cartridge of any one or more of Examples 1 through 3, wherein the clearance channel is positioned radially outward from and adjacent to the circular path of the track.

Example 5

The needle cartridge of any one or more of Examples 1 through 4, wherein the clearance channel surrounds the track about the circular path.

Example 6

The needle cartridge of any one or more of Examples 1 through 5, wherein the needle cover further defines the circular path such that the arcuate needle is positioned along the circular path between the needle cover and the cartridge body within the track.

Example 7

The needle cartridge of any one or more of Examples 1 through 6, wherein the needle cover further defines the suture path such that the suture thread is configured to be received along the suture path between the needle cover and the cartridge body within the clearance channel.

Example 8

The needle cartridge of any one or more of Examples 1 through 7, wherein the circular path has a needle gap height between the needle cover and the cartridge body through the track, wherein the suture path has a suture gap height between the needle cover and the cartridge body through the clearance channel, and wherein the suture gap height is less than the needle gap height.

Example 9

The needle cartridge of Example 8, wherein the suture gap height is less than one-half of the needle gap height.

Example 10

The needle cartridge of any one or more of Examples 1 through 9, wherein the suture path has a radial cross-sectional suture gap area, wherein the suture thread has a transverse cross-sectional thread area, wherein the transverse cross-sectional thread area is configured to pass through the radial cross-sectional suture gap area in parallel with the radial cross-sectional suture gap area such that the arcuate needle is configured to orbit as the suture thread simultaneously passes through the clearance channel.

Example 11

The needle cartridge of Example 10, wherein the radial cross-sectional suture gap area is greater than or substantially similar to the transverse cross-sectional thread area such that the arcuate needle is configured to orbit as the suture thread simultaneously passes through the clearance channel.

Example 12

The needle cartridge of Example 11, wherein the radial cross-sectional suture gap area is substantially similar to the transverse cross-sectional thread area such that the arcuate needle is configured to orbit as the suture thread simultaneously passes through the clearance channel.

Example 13

The needle cartridge of Example 10, wherein the radial cross-sectional suture gap area is continuous along an entirety of the clearance channel.

Example 14

The needle cartridge of any one or more of Examples 1 through 13, wherein the arcuate needle is configured to orbit within an orbital plane, and wherein the clearance channel extends in a channel plane in parallel with the orbital plane.

Example 15

The needle cartridge of Example 14, wherein the channel plane is offset from orbital plane such that the clearance channel is adjacent to the needle cover.

Example 16

A surgical suturing instrument comprising: (a) a body; (b) a shaft assembly extending distally from the body; (c) a cartridge receiving assembly disposed at a distal end portion of the shaft assembly; and (d) a needle cartridge configured to be coupled with the cartridge receiving assembly, the needle cartridge comprising: (i) a cartridge body; (ii) a track extending through at least a portion of the cartridge body and at least partially defining a circular path; (iii) an arcuate needle movably positioned within the track and having a leading end and a trailing end; (iv) a suture thread extending from the trailing end; (v) a needle driver operatively connected to the cartridge body and the arcuate needle, wherein the needle driver is configured to orbit the arcuate needle along the circular path; (vi) a needle cover secured to the cartridge body and configured to releasably retain the arcuate needle with the track; and (vii) a clearance channel extending through at least a portion of the cartridge body along the track in communication with the track such that the clearance channel at least partially defines a suture path, wherein the suture path is configured to receive the suture thread extending from the trailing end of the arcuate needle as the arcuate needle moves along the circular path thereby inhibiting the suture thread from obstructing movement of the arcuate needle.

Example 17

The needle cartridge of Example 16, wherein the needle cover further defines the circular path such that the arcuate needle is positioned along the circular path between the needle cover and the cartridge body within the track.

Example 18

The needle cartridge of any one or more of Examples 16 through 17, wherein the circular path has a needle gap height between the needle cover and the cartridge body through the track, wherein the suture path has a suture gap height between the needle cover and the cartridge body through the clearance channel, and wherein the suture gap height is less than the needle gap height.

Example 19

The needle cartridge of Example 18, wherein the suture path has a radial cross-sectional suture gap area, wherein the suture thread has a transverse cross-sectional thread area, wherein the transverse cross-sectional thread area is configured to pass through the radial cross-sectional suture gap area in parallel with the radial cross-sectional suture gap area such that the arcuate needle is configured to orbit as the suture thread simultaneously passes through the clearance channel.

Example 20

A method of orbiting an arcuate needle of a needle cartridge within a surgical suturing instrument, wherein the needle cartridge includes a cartridge body; a track extending through at least a portion of the cartridge body and at least partially defining a circular path; the arcuate needle movably positioned within the track and having a leading end and a trailing end; a suture thread extending from the trailing end; a needle driver operatively connected to the cartridge body and the arcuate needle, wherein the needle driver is configured to orbit the arcuate needle along the circular path; a needle cover secured to the cartridge body and configured to releasably retain the arcuate needle with the track; and a clearance channel extending through at least a portion of the cartridge body and along the track in communication with the track such that the clearance channel at least partially defines a suture path, wherein the suture path is configured to receive the suture thread extending from the trailing end of the arcuate needle as the arcuate needle moves along the circular path, the method comprising: (a) orbiting the arcuate needle along the circular path through the track and simultaneously introducing the suture thread into the clearance channel along the suture path thereby inhibiting the suture thread from obstructing movement of the arcuate needle.

IV. MISCELLANEOUS

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein, is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A needle cartridge for a surgical suturing instrument, the needle cartridge comprising:
   (a) a cartridge body;
   (b) a track extending through at least a portion of the cartridge body and at least partially defining a circular path;
   (c) an arcuate needle movably positioned within the track and having a leading end and a trailing end;
   (d) a suture thread extending from the trailing end;
   (e) a needle driver operatively connected to the cartridge body and the arcuate needle, wherein the needle driver is configured to orbit the arcuate needle along the circular path;
   (g) a needle cover secured to the cartridge body and configured to releasably retain the arcuate needle with the track; and
   (g) a clearance channel extending through at least a portion of the cartridge body along the track in communication with the track such that the clearance channel at least partially defines a suture path,
   wherein the suture path is configured to receive the suture thread extending from the trailing end of the arcuate needle as the arcuate needle moves along the circular path thereby inhibiting the suture thread from obstructing movement of the arcuate needle,
   wherein the clearance channel is positioned radially outward from and adjacent to the circular path of the track, wherein the clearance channel surrounds the track about the circular path.

2. The needle cartridge of claim 1, wherein the track includes a track inlet opening, wherein the leading end of the arcuate needle is configured to be introduced into the track through the track inlet opening, wherein the clearance channel includes a clearance inlet opening configured to receive the suture thread therein, wherein the clearance inlet opening is positioned adjacent to the track inlet opening such that the clearance inlet opening is in direct communication with the track inlet opening.

3. The needle cartridge of claim 2, wherein the track further includes a track outlet opening, wherein the trailing end of the arcuate needle is configured to be discharged from the track through the track outlet opening, wherein the clearance channel further includes a clearance outlet opening configured to discharge the suture thread therefrom, and wherein the clearance outlet opening is positioned adjacent to the track outlet opening such that the clearance outlet opening is in direct communication with the track outlet opening.

4. The needle cartridge of claim 1, wherein the needle cover further defines the circular path such that the arcuate needle is positioned along the circular path between the needle cover and the cartridge body within the track.

5. The needle cartridge of claim 4, wherein the needle cover further defines the suture path such that the suture thread is configured to be received along the suture path between the needle cover and the cartridge body within the clearance channel.

6. The needle cartridge of claim 1, wherein the circular path has a needle gap height between the needle cover and the cartridge body through the track, wherein the suture path has a suture gap height between the needle cover and the cartridge body through the clearance channel, and wherein the suture gap height is less than the needle gap height.

7. The needle cartridge of claim 6, wherein the suture gap height is less than one-half of the needle gap height.

8. The needle cartridge of claim 1, wherein the suture path has a radial cross-sectional suture gap area, wherein the suture thread has a transverse cross-sectional thread area, wherein the transverse cross-sectional thread area is configured to pass through the radial cross-sectional suture gap area in parallel with the radial cross-sectional suture gap area such that the arcuate needle is configured to orbit as the suture thread simultaneously passes through the clearance channel.

9. The needle cartridge of claim 8, wherein the radial cross-sectional suture gap area is greater than or substantially similar to the transverse cross-sectional thread area such that the arcuate needle is configured to orbit as the suture thread simultaneously passes through the clearance channel.

10. The needle cartridge of claim 9, wherein the radial cross-sectional suture gap area is substantially similar to the transverse cross-sectional thread area such that the arcuate needle is configured to orbit as the suture thread simultaneously passes through the clearance channel.

11. The needle cartridge of claim 8, wherein the radial cross-sectional suture gap area is continuous along an entirety of the clearance channel.

12. The needle cartridge of claim 1, wherein the arcuate needle is configured to orbit within an orbital plane, and wherein the clearance channel extends in a channel plane in parallel with the orbital plane.

13. The needle cartridge of claim 12, wherein the channel plane is offset from the orbital plane such that the clearance channel is adjacent to the needle cover.

14. A surgical suturing instrument comprising:
   (a) a body;
   (b) a shaft assembly extending distally from the body;
   (c) a cartridge receiving assembly disposed at a distal end portion of the shaft assembly; and
   (d) a needle cartridge configured to be coupled with the cartridge receiving assembly, the needle cartridge comprising:
      (i) a cartridge body;
      (ii) a track extending through at least a portion of the cartridge body and at least partially defining a circular path;
      (iii) an arcuate needle movably positioned within the track and having a leading end and a trailing end;
      (iv) a suture thread extending from the trailing end;
      (v) a needle driver operatively connected to the cartridge body and the arcuate needle, wherein the needle driver is configured to orbit the arcuate needle along the circular path;

(vi) a needle cover secured to the cartridge body and configured to releasably retain the arcuate needle with the track; and (vii) a clearance channel extending through at least a portion of the cartridge body along the track in communication with the track such that the clearance channel at least partially defines a suture path, wherein the suture path is configured to receive the suture thread extending from the trailing end of the arcuate needle as the arcuate needle moves along the circular path thereby inhibiting the suture thread from obstructing movement of the arcuate needle, wherein the needle cover further defines the circular path such that the arcuate needle is positioned along the circular path between the needle cover and the cartridge body within the track, wherein the circular path has a needle gap height between the needle cover and the cartridge body through the track, wherein the suture path has a suture gap height between the needle cover and the cartridge body through the clearance channel, and wherein the suture gap height is less than the needle gap height.

15. The needle cartridge of claim 14, wherein the suture path has a radial cross-sectional suture gap area, wherein the suture thread has a transverse cross-sectional thread area, wherein the transverse cross-sectional thread area is configured to pass through the radial cross-sectional suture gap area in parallel with the radial cross-sectional suture gap area such that the arcuate needle is configured to orbit as the suture thread simultaneously passes through the clearance channel.

16. A method of orbiting an arcuate needle of a needle cartridge within a surgical suturing instrument, wherein the needle cartridge includes a cartridge body; a track extending through at least a portion of the cartridge body and at least partially defining a circular path; the arcuate needle movably positioned within the track and having a leading end and a trailing end; a suture thread extending from the trailing end; a needle driver operatively connected to the cartridge body and the arcuate needle, wherein the needle driver is configured to orbit the arcuate needle along the circular path; a needle cover secured to the cartridge body and configured to releasably retain the arcuate needle with the track; and a clearance channel extending through at least a portion of the cartridge body and along the track in communication with the track such that the clearance channel at least partially defines a suture path, wherein the suture path is configured to receive the suture thread extending from the trailing end of the arcuate needle as the arcuate needle moves along the circular path, the method comprising:

(a) orbiting the arcuate needle along the circular path through the track and simultaneously introducing the suture thread into the clearance channel along the suture path such that the suture thread is radially outward from the circular path thereby inhibiting the suture thread from obstructing movement of the arcuate needle.

17. The needle cartridge of claim 1, further comprising a ledge positioned between the clearance channel and the track.

18. The needle cartridge of claim 1, wherein the clearance channel and the track are concentric.

19. The surgical suturing instrument of claim 14, wherein the cartridge body includes first and second surfaces offset from each other, wherein the needle gap height is defined between the needle cover and the first surface, wherein the suture gap height is defined between the needle cover and the second surface.

20. The method of claim 16, wherein introducing the suture thread into the clearance channel includes extending the suture thread from the track into the clearance channel.

* * * * *